(12) United States Patent
Heyes (10) Patent No.: US 10,076,597 B2
(45) Date of Patent: Sep. 18, 2018

(54) DIALYSIS MACHINE

(75) Inventor: Keith Heyes, Barnt Green (GB)

(73) Assignee: Quanta Fluid Systems Ltd., Warwickshire (GB)

( * ) Notice: Subject to any disclaimer, the term of this patent is extended or adjusted under 35 U.S.C. 154(b) by 723 days.

(21) Appl. No.: 14/374,756

(22) PCT Filed: Feb. 2, 2012

(86) PCT No.: PCT/GB2012/000113
§ 371 (c)(1),
(2), (4) Date: Sep. 8, 2014

(87) PCT Pub. No.: WO2013/114063
PCT Pub. Date: Aug. 8, 2013

(65) Prior Publication Data
US 2015/0041377 A1    Feb. 12, 2015

(51) Int. Cl.
*A61M 1/16* (2006.01)

(52) U.S. Cl.
CPC ....... *A61M 1/1656* (2013.01); *A61M 2205/12* (2013.01)

(58) Field of Classification Search
None
See application file for complete search history.

(56) References Cited

U.S. PATENT DOCUMENTS 4,161,264 A * 7/1979 Malmgren .......... A61M 1/1656
222/135

FOREIGN PATENT DOCUMENTS

| WO | WO 2006/120415 A1 | 11/2006 | |
|----|---|---|---|
| WO | WO 2006120415 A1 * | 11/2006 | .......... A61M 1/1656 |
| WO | WO 2010/146343 A2 | 12/2010 | |

OTHER PUBLICATIONS

Oct. 5, 2012 International Search Report for PCT/GB2012/000113.
Aug. 14, 2014 Transmittal of International Preliminary Report on Patentability of PCT/GB2012/000113.

* cited by examiner

*Primary Examiner* — Michael J Felton
*Assistant Examiner* — Katherine Will
(74) *Attorney, Agent, or Firm* — Hahn Loeser & Parks LLP (57) ABSTRACT

A hemodialysis machine including a cartridge which defines a fluid pathway for delivering a dialysate solution base to a mixing pump, a main body having a platen which, in use, abuts the cartridge, the cartridge having a chassis with a platen side covered by a deformable membrane which, in use, abuts the platen, the chassis and membrane defining the flow path, the flow path including a dialysate base solution pump chamber, the platen having a dialysate base solution pump cavity which, collectively with the dialysate base solution pump chamber, forms a dialysate base solution pump for pumping dialysate base solution to the mixing pump by actuation of the membrane, wherein the volume of the dialysate base solution pump cavity is variable so as to allow a variation in the volume of dialysate base solution pumped from the dialysate base solution pump chamber to the mixing pump chamber on each stroke of the solution pump.

15 Claims, 7 Drawing Sheets

DIALYSIS MACHINE

The present application is a § 371submission of international application no. PCT/GB2012/000113, which was filed on 2 Feb. 2012 and entitled Dialysis Machine, and which was published in the English language on 8 Aug. 2013 with publication no. WO 2013/114063 A1.

The present invention relates to dialysis machines and in particular, but not exclusively, to a disposable cartridge for use in hemodialysis machine.

Dialysis is a treatment which replaces the renal function of removing excess fluid and waste products, such as potassium and urea, from blood. The treatment is either employed when renal function has deteriorated to an extent that uremic syndrome becomes a threat to the body's physiology (acute renal failure) or, when a longstanding renal condition impairs the performance of the kidneys (chronic renal failure).

There are two major types of dialysis, namely hemodialysis and peritoneal dialysis.

In peritoneal dialysis treatment, a dialysate solution is run through a tube into the peritoneal cavity. The fluid is left in the cavity for a period of time in order to absorb the waste products, and is subsequently removed through the tube for disposal.

It is common for patients in the early stages of treatment for a longstanding renal condition to be treated by peritoneal dialysis before progressing to hemodialysis at a later stage.

In hemodialysis, the patient's blood is removed from the body by an arterial line, is treated by the dialysis machine, and is then returned to the body by a venous line. The machine passes the blood through a dialyser containing tubes formed from a semi permeable membrane. On the exterior of the semi permeable membrane is a dialysate solution. The semi permeable membrane filters the waste products and excess fluid from the blood into the dialysate solution. The membrane allows the waste and a controlled volume of fluid to permeate into the dialysate whilst preventing the loss of larger more desirable molecules, like blood cells and certain proteins and polypeptides.

The action of dialysis across the membrane is achieved primarily by a combination of diffusion (the migration of molecules by random motion from a region of higher concentration to a region of lower concentration), and convection (solute movement that results from bulk movement of solvent, usually in response to differences in hydrostatic pressure).

Fluid removal (otherwise known as ultrafiltration) is achieved by altering the hydrostatic pressure of the dialysate side of the membrane, causing free water to move across the membrane along the pressure gradient.

The correction of uremic acidosis of the blood is achieved by use of a bicarbonate buffer. The bicarbonate buffer also allows the correction of the blood bicarbonate level.

The dialysis solution consists of a sterilized solution of mineral ions. These ions are contained within an acid buffer which is mixed with the serilised water and bicarbonate base prior to delivery to the dialyser.

Dialysate composition is critical to successful dialysis treatment since the level of dialytic exchange across the membrane, and thus the possibility to restore adequate body electrolytic concentrations and acid-base equilibrium, depends on the composition.

The correct composition is accomplished primarily by formulating a dialysate whose constituent concentrations are set to approximate normal values in the body.

However, achieving the correct composition of dialysate requires the accurate control of low volumes of liquid and at present this is achieved by the provision of complex fluid paths, including multiple pumping and valving components on the dialysis machine.

This adds cost and complexity to the machine and necessitates the sterilisation of the fluid paths, and pumping and valving components between treatments.

The provision of a dialysate cartridge which can be disposed of after a treatment offers a solution to this problem but presents additional technical challenges in terms of achieving an accurate composition of dialysate on the cartridge.

It is an object of the present invention to provide a hemodialysis machine which at least mitigates some of the problems described above.

According to a first aspect of the invention there is provided a hemodialysis machine including a cartridge which defines a fluid pathway for delivering a dialysate solution base to a mixing pump, a main body having a platen which, in use, abuts the cartridge, the cartridge having a chassis with a platen side covered by a deformable membrane which, in use, abuts the platen, the chassis and membrane defining the flow path, the flow path including a dialysate base solution pump chamber, the platen having a dialysate base solution pump cavity which, collectively with the dialysate base solution pump chamber, forms a dialysate base solution pump for pumping dialysate base solution to the mixing pump by actuation of the membrane, wherein the volume of the dialysate base solution pump cavity is variable so as to allow a variation in the volume of dialysate base solution pumped from the dialysate base solution pump chamber to the mixing pump chamber.

Advantageously, by altering the volume of the dialysate base solution pump cavity, the volume of dialysate base solution pumped from the dialysate base solution pump into the mixing pump on each stroke of the solution pump can be easily altered without the need to alter the pressure or stroke rate of the dialysate base solution membrane pump. In this way the machine can continually provide an accurate composition of dialysate solution without the need for additional membrane actuation control. This allows for an accurate formation of dialysate solution on the cartridge without the need for altering the pneumatic control of the membrane actuation which would add cost and complexity to the machine.

Preferably, the flow path further includes a mixing pump cavity which, collectively with the mixing pump chamber, forms a mixing pump for pumping dialysate fluid to the dialyser.

Preferably, the dialysate base solution pump cavity is defined in part by a piston, the piston being moveable with respect to the platen to vary the volume of the dialysate base solution pump cavity.

Preferably, the piston is moveable into and out of the dialysate base solution pump cavity to vary the volume of the dialysate base solution pump cavity.

Preferably, the piston is moved by a stepper motor mount in the main body.

Preferably, the flow path includes a flow balance pump for pumping dialysate into and out of the dialyser, the flow balance pump defined collectively by a flow balance pump chamber in the cartridge and a flow balance pump cavity in the platen.

Preferably, the flow balance pump comprises a first flow balance pump upstream of the dialyser and a second flow balance pump downstream of the dialyser.

Preferably, the mixing pump comprises a first mixing pump and the dialysate base solution pump comprises a bicarbonate base solution pump, the first mixing pump for receiving water from a water source and a bicarbonate base solution from the bicarbonate base solution pump and pumping out a water/bicarbonate mix, the machine further including a second dialysate base solution pump which comprises an acid base solution pump and a second mixing pump for receiving the water/bicarbonate mix and an acid base solution from the second dialysate base solution pump and pumping out a fully mixed dialysate solution to the dialyser.

Preferably, the second mixing pump pumps dialysate solution to the first flow balance pump.

Preferably, the machine includes a conductivity sensor in the flow path downstream of the or each mixing pump.

Preferably, the piston is moved in response to a change in the conductivity of the fluid pumped out of the or each mixing pump.

Figure 1:
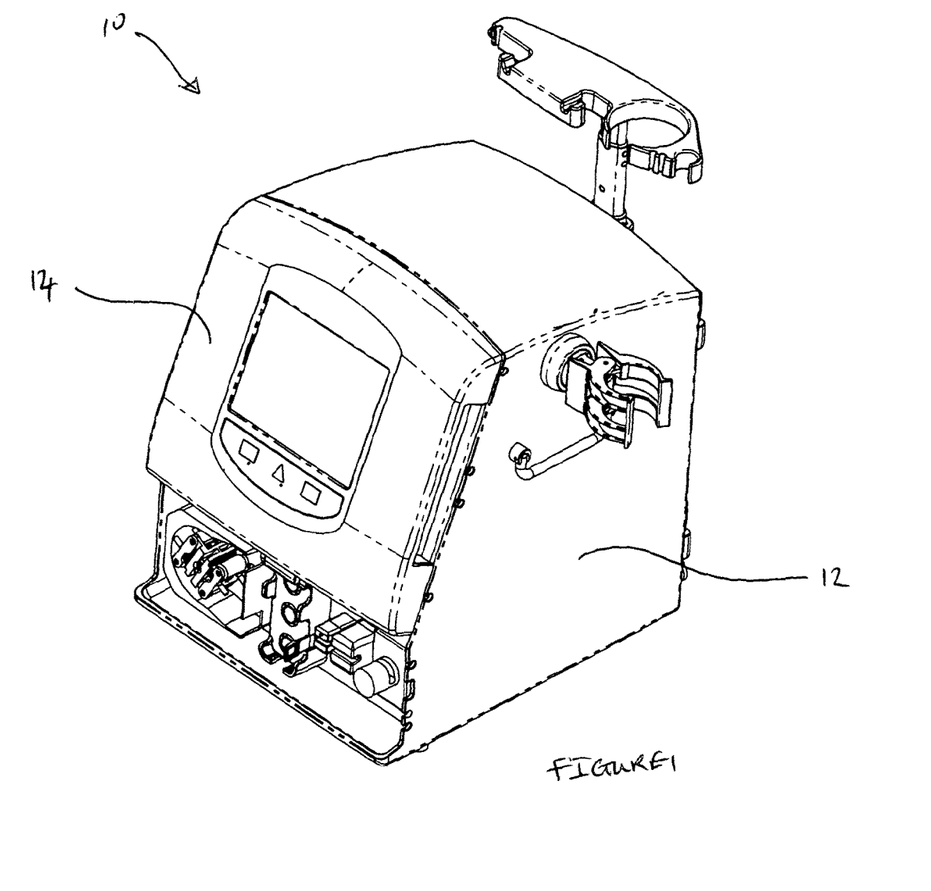
FIG. 1 is an isometric view of a dialysis machine including the cartridge according to the present invention.

Referring to FIG. 1, a dialysis machine 10 is shown having a main body 12 and a hinged door 14. The door 14 is hinged so as to allow a dialysis cartridge 16 (see FIG. 2) to be received between the main body 12 and the door 14 before the door is closed to engage the cartridge.

The main body 12 has an engine portion which includes a pneumatic compressor for operating the cartridge 16 and a series of sensors for sensing various parameters on the cartridge 16, as will be discussed in further detail below.

The cartridge 16 will now be described in further detail with reference initially to FIG. 2. The cartridge 16 has a platen side 18 (shown in FIG. 4) and a patient side 20 (shown in FIG. 3). The platen side 18 engages the platen on the main body 12 of the machine 10, as will be described in further detail below, and the patient side engages the door 14 of the machine so that it faces the patient during use. The cartridge is form from an acrylic such as SG-10 which is moulded in two parts (a platen side and a patient side) before being bonded together. In this way a series of flow paths are formed in the cartridge for carrying dialysate and its constituent parts of water, bicarbonate solution and acid solution. Both the platen side 18 and patient side 20 are covered in a clear flexible membrane 13 formed from, for example, DEHP-free PVC which is operable by pneumatic pressure applied to the membrane by the pneumatic compressor in the main body. The cartridge has four pump chambers and a series of valves, as will be described in further detail below, to allow the machine to control a flow of water, bicarbonate solution and acid solution on the cartridge to mix and pump dialysate solution to and from a dialyser.

A platen 21 (see FIGS. 5 and 6) in the main body 12 of the machine 10 selectively applies either a positive or negative pressure to the membrane in order to selectively open and close valves and to pump fluid into or from the pump chambers. The fluid flow through the cartridge will now be described before the mode of operation of the pumps and valves is explained in detail.

Figure 2:
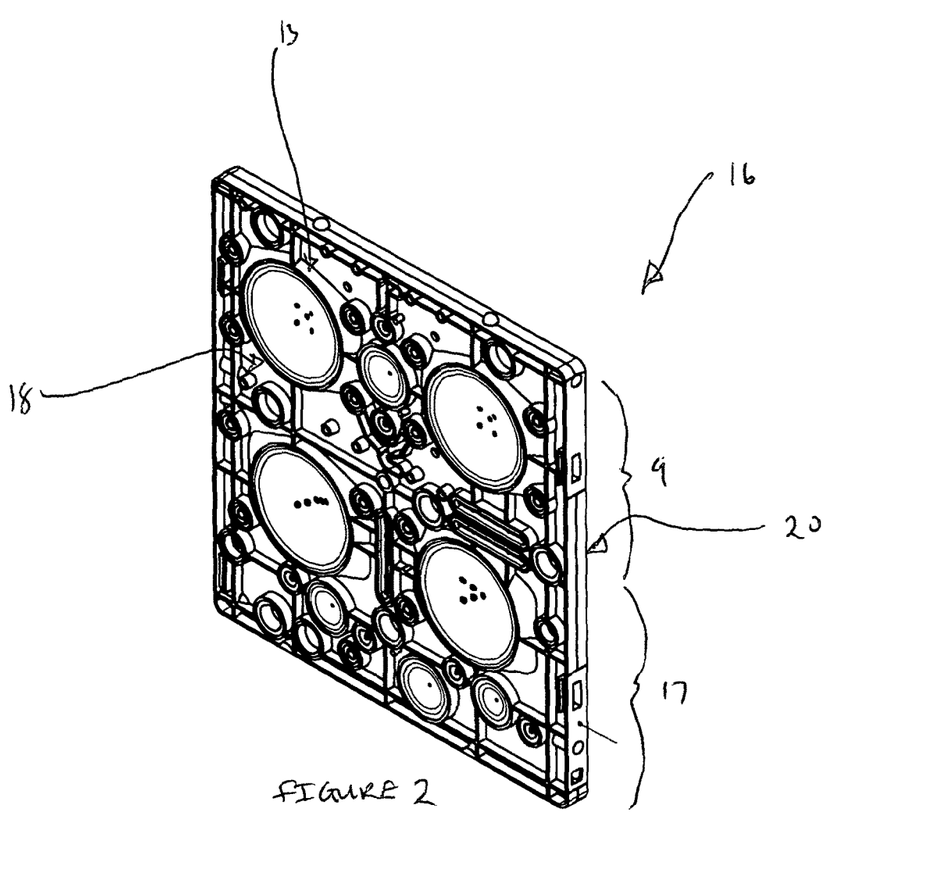
FIG. 2 is an isometric view of cartridge of the machine of FIG. 1.

The cartridge 16 has a dialysate mixing portion indicated generally at 17 in FIG. 2 and a flow balancer indicated generally at 19 in FIG. 2. The purpose of the mixing portion is to deliver accurately mixed homogeneous dialysate solution to the flow balancer which is provided to ensure that the flow of fluid supplied to the dialyser matches (to within clinical tolerances) the volume of fluid drawn from the dialyser. Accurate flow balance is critical to effective and safe treatment of the patient.

Dialysate Mixing

Dialysate is mixed on the cartridge by combining water with two dialysate base solutions, namely a bicarbonate solution and an acid solution. This process will now be described in further detail.

Figure 3:
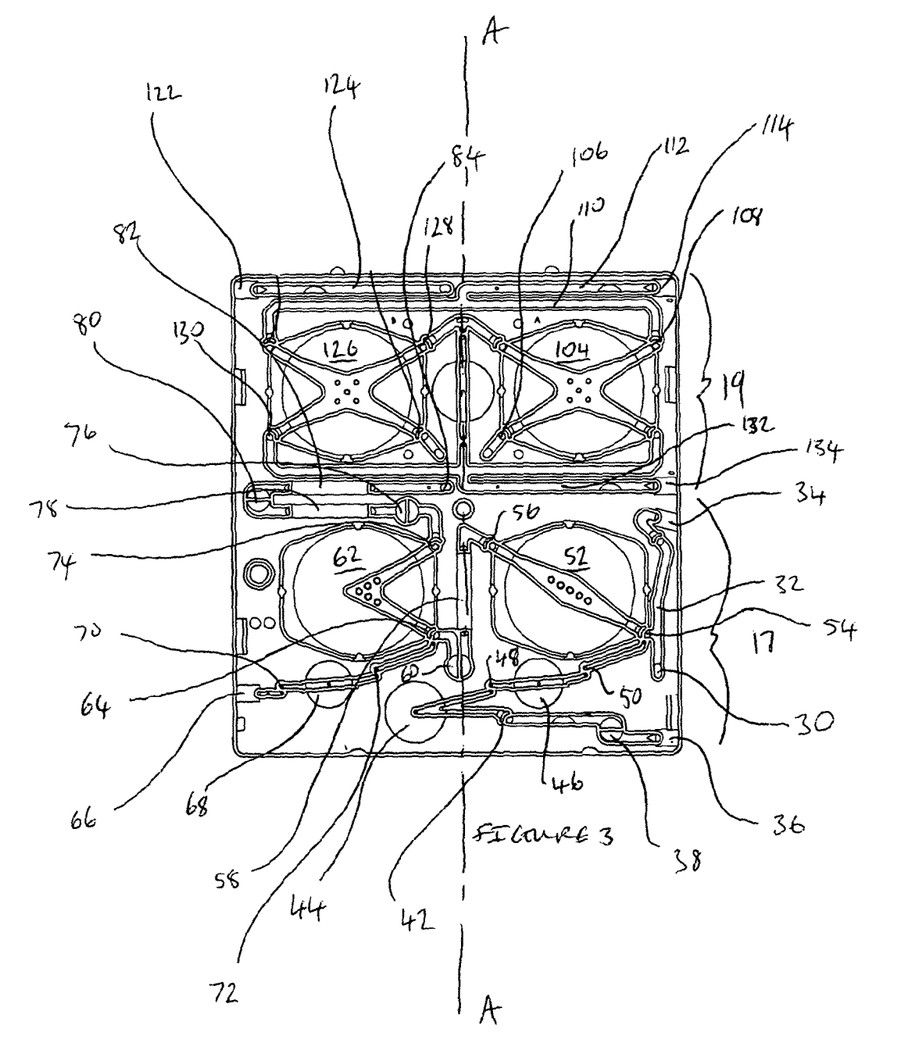
FIG. 3 is a plan view of the door side of the cartridge of FIG. 2.
Figure 4:
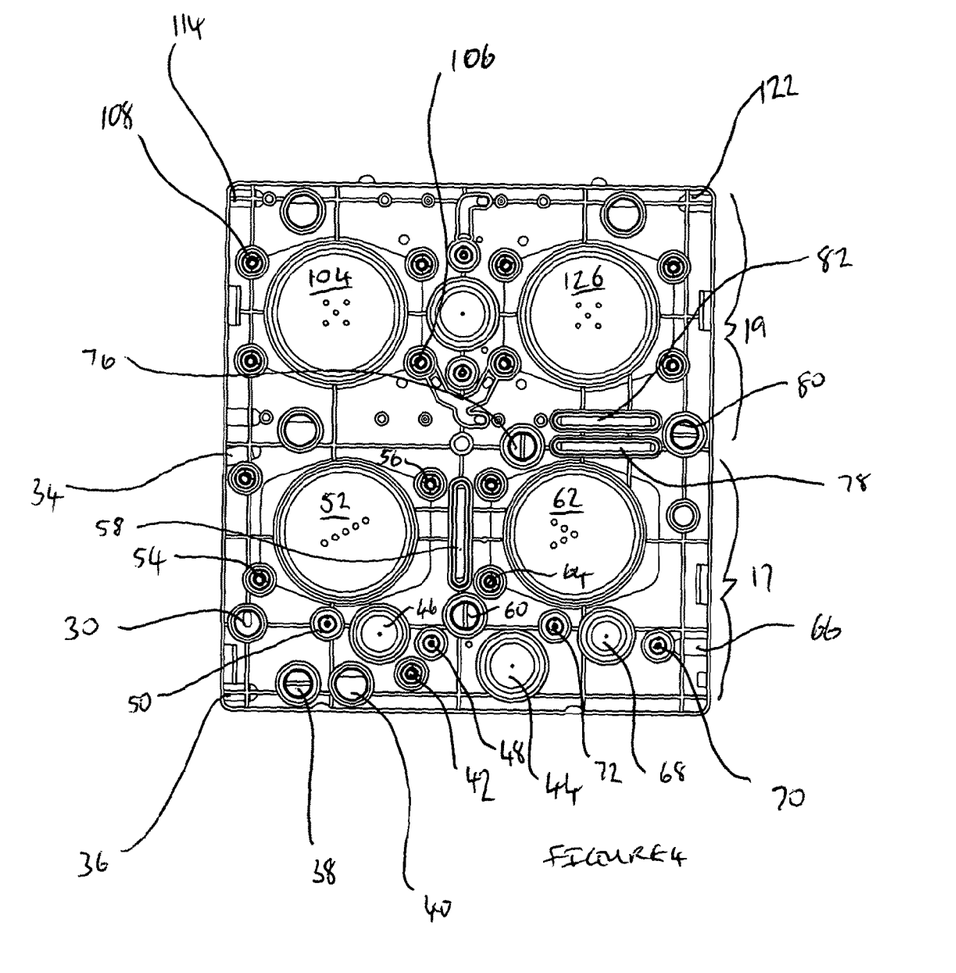
FIG. 4 is a plan view of the platen side of the cartridge of FIG. 2.

Referring now to FIGS. 3 and 4, dialysate solution is mixed in the mixing portion 17 of the cartridge 16 as follows. Reverse osmosis (RO) water is admitted onto the cartridge via RO water inlet port 30. Water passes up channel 32 and exits the cartridge 16 at RO water outlet port 34. From here the water is carried via a tube (not shown for clarity) and passes through a bicarbonate cartridge in a known manner to generate a bicarbonate solution. The bicarbonate solution is admitted onto the cartridge 16 via bicarbonate inlet port 36. The temperature of the bicarbonate solution is measured at sensing port 38 and the bicarbonate solution pressure is measured at sensing port 40 (FIG. 4 only). The bicarbonate solution passes a bicarbonate control valve 42 before entering a bicarbonate solution reservoir 44. A first dialysate base solution pump chamber in the form of a bicarbonate dosing pump chamber 46 has an associated inlet valve 48 and outlet valve 50. From the outlet valve 50 the bicarbonate solution passes to a first mixing pump chamber in the form of a bicarbonate pump chamber 52 via bicarbonate pump inlet valve 54. The bicarbonate pump inlet valve 54 also admits RO water into the bicarbonate pump chamber 52 from the RO water inlet port 30. In this way RO water and bicarbonate solution can be admitted into the bicarbonate pump chamber 52 for subsequent pumping out of the bicarbonate pump chamber 52 of a mixed bicarbonate and water solution (called bicarbonate mixture from hereon in for ease of reference) via a bicarbonate pump outlet valve 56. From the bicarbonate pump outlet valve 56 the bicarbonate mixture enters a bicarbonate mixture sensor channel 58 in which the machine 12 measures the conductivity of the mixture in a known manner. The mixture then enters a bicarbonate mixture temperature sensor 60 before entering a second mixing pump chamber in the form of an acid pump chamber 62 via acid pump inlet valve 64. Also admitted into the acid pump chamber 62 is an acid solution which enters the cartridge from a known bagged supply (not shown for clarity) at an acid solution inlet port 66. From the acid inlet port 66 the acid solution passes through a second dialysate base solution pump chamber in the form of an acid dosing pump chamber 68 via acid dosing pump chamber inlet valve 70 and an outlet valve 72. In this way bicarbonate mixture and acid solution are admitted into the acid pump chamber 62 for subsequent pumping out of the pump chamber 62 of a fully mixed dialysate solution via an acid pump outlet valve 74. From here the fully mixed dialysate solution passes through a first dialysate temperature sensor 76 and first dialysate conductivity sensor 78. A second dialysate temperature sensor 80 and second dialysate conductivity sensor 82 are provided to corroborate the data provided by the first sensors 76, 78.

Fully mixed dialysate solution then passes through aperture 84 (shown in FIG. 3 only) to be received by the flow balance portion 19 of the cartridge 16.

Flow Balance

The flow balancer 19 is mirrored about centreline A-A as shown in FIG. 3. The flow balancer 19 will be described in relation to FIGS. 2 and 3.

Dialysate solution passes from the aperture 84 into the first flow balance pump chamber 104 through inlet valve 106 upon the actuation of the membrane by the machine 10 to draw the dialysate into the pump chamber of pump 104. The dialysate solution is then pumped out of the pump chamber 104 via outlet valve 108 upon the closure of the inlet valve 106. The dialysate solution then passes down a channel 110 before passing into a dialyser outlet channel 112. From there the dialysate solution exits the cartridge via dialyser outlet 114 and is carried to a dialyser (not shown for clarity).

The dialysate solution returns to the cartridge from the dialyser via a tubing set (also not shown for clarity). A second flow balance pump chamber 126 is actuated to draw the dialysate solution through the inlet 122, down dialyser inlet channel 124, passed the second flow balance pump inlet valve 128 and into the pump chamber 126. The dialysate solution is then pumped out of the pump chamber 126 via an outlet valve 130 upon the closure of the inlet valve 128. The dialysate solution then passes down a drain outlet channel 132. From there the dialysate solution exits the cartridge via drain outlet 134 and is carried to a drain (not shown for clarity).

The operation of the first and second flow balance pumps can be switched by virtue of the mirroring of the valves and pump chambers. In this way the first flow balance pump 104 is also used to draw dialysate solution form the dialyser 118 and the second flow balance pump 126 is used to pump dialysate solution into the dialyser 118. This allows the pumps to switch over the course of a treatment ensuring that any geometric variance between the first and second pump chambers is balanced out.

Control of Dialysate Mixing

In use the volume of bicarbonate and acid solution mixed with the RO water must be closely monitored and controlled in order to achieve effective treatment. The monitoring is achieved in a known manner using conductivity sensors 78, 82 (see FIG. 3). In the present invention the conductivity signal generated by these sensors (which is indicative of the strength of the admixture) is used to control the volume of bicarbonate solution pumped through the bicarbonate dosing pump chamber 46 into the bicarbonate pump chamber 52 and the volume of acid solution pumped through the acid dosing pump chamber 68 into the acid pump chamber 62 as follows.

Figure 5:
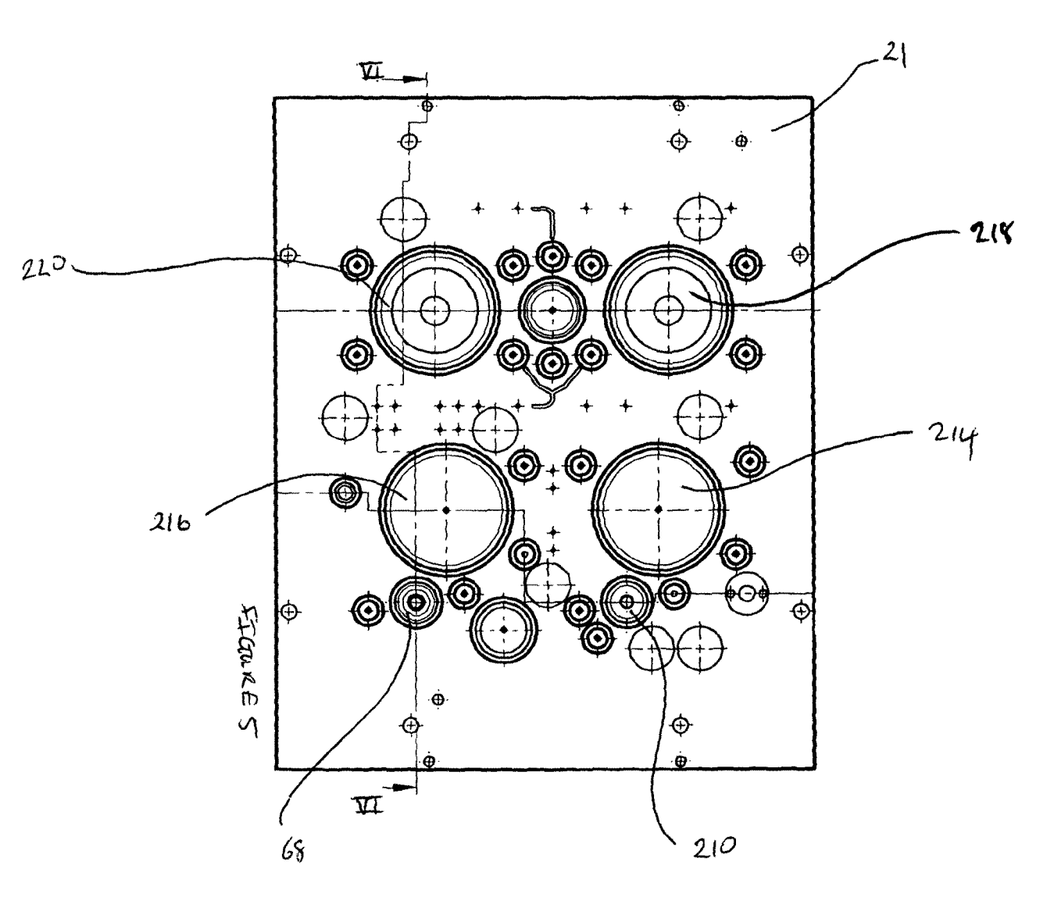
FIG. 5 is a plan view of the platen of the machine of FIG. 1.

Referring to FIG. 5 the platen 21 has features which correspond to the features on the cartridge 16. The platen 21 has the following features:

a first dialysate base solution pump cavity in the form of bicarbonate dosing pump cavity 210 which corresponds to the bicarbonate dosing pump chamber 46 on the cartridge 16 and which together form a first dialysate base solution pump;

a second dialysate base solution pump cavity in the form of an acid dosing pump cavity 212 which corresponds to the acid dosing pump chamber 68 on the cartridge 16 which together form a first dialysate base solution pump;

a first mixing pump cavity in the form of a bicarbonate pump cavity 214 which corresponds to the bicarbonate pump chamber 52 on the cartridge 16 which together form a first mixing pump;

a second mixing pump cavity in the form of an acid pump cavity 216 which corresponds to the acid pump chamber 62 on the cartridge 16 which together form a second mixing pump;

a first flow balance pump cavity 218 which corresponds to the first flow balance pump chamber 104 on the cartridge 16 which together form a first flow balance pump; and a second flow balance pump cavity 220 which corresponds to the second flow balance pump chamber 126 on the cartridge 16 which together form a second flow balance pump.

Figure 6:
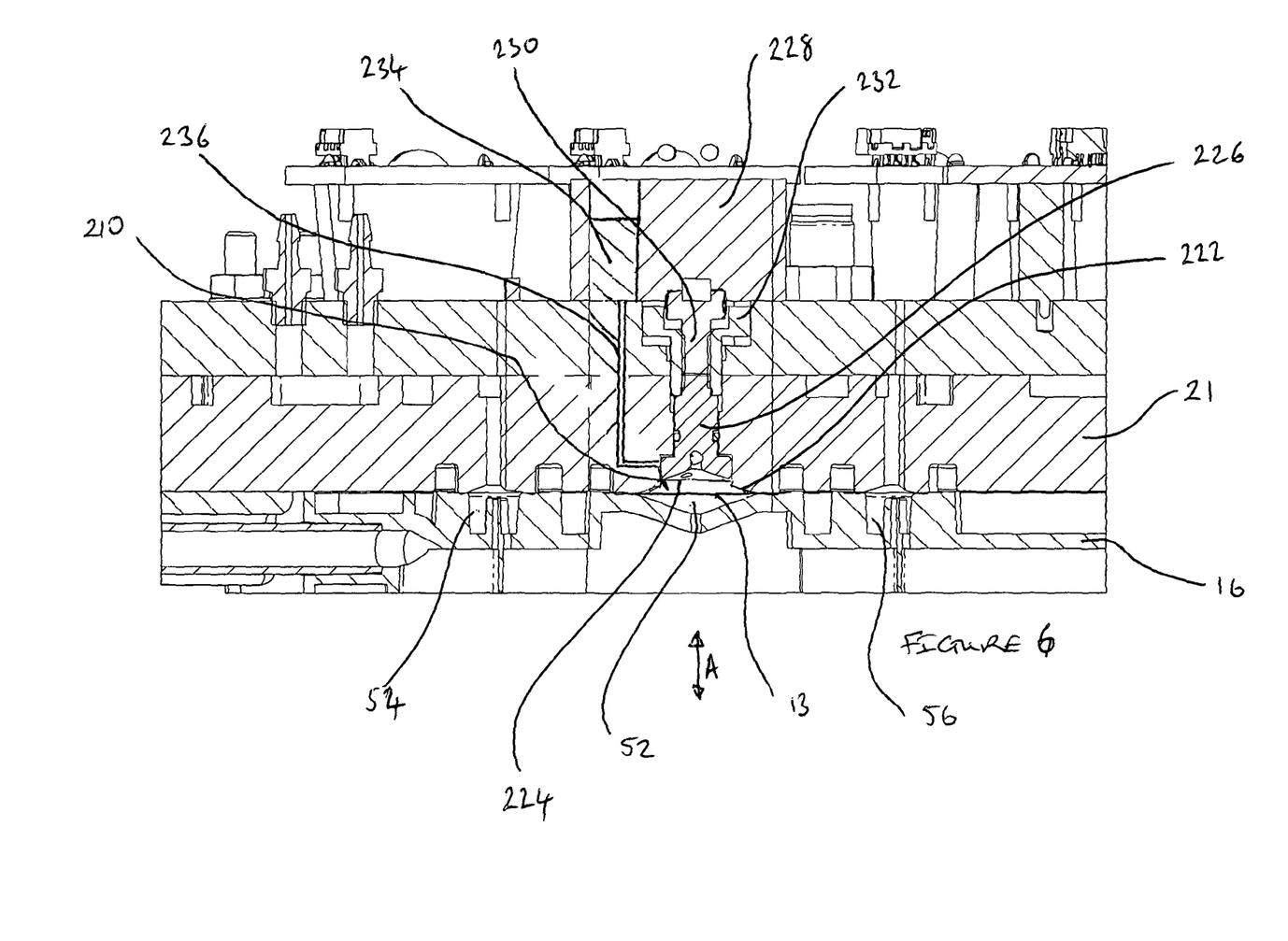
FIG. 6 is sectioned side view of the platen of FIG. 5 taken along line VI-VI in FIG. 5.

Referring to 6, the cartridge 16 is shown retained against the platen 21 by a door (not shown in FIG. 6 for clarity). The bicarbonate dosing pump cavity 210 is shown opposite the bicarbonate pump chamber 52 separated by the membrane 13. The bicarbonate dosing pump cavity 210 is formed by an outer portion 222 defined by the platen 21 and an inner portion 224 defined by a piston 226 housed within the platen 21. The piston 226 is able to move within the platen in direction A under the action of a stepper motor 228. The stepper motor 228 drives a threaded screw 230 which rotates to move the piston 226 by way of an intermediate threaded collar 232. Pressure and vacuum is applied to the membrane 13 by pneumatic valve 234 via pneumatic line 236.

In use the valve 234 applies a negative pressure to the side of the membrane facing the platen 21 via pneumatic line 236 to draw bicarbonate solution into the pump. The valve 234 subsequently applies a positive pressure to the membrane 13 in order to pump bicarbonate solution out of the pump chamber. In this way the membrane 13 is alternately drawn into the bicarbonate dosing pump cavity 210 to draw bicarbonate solution into the bicarbonate pump chamber 52 and forced into the bicarbonate pump chamber 52 to pump bicarbonate solution out of the pump chamber. In the present invention the volume of fluid pumped out of the bicarbonate pump chamber 52 is determined by the size of the bicarbonate dosing pump cavity 210 which can be varied in response to the conductivity of the bicarbonate solution measured by sensor 78 as follows.

Figure 7:
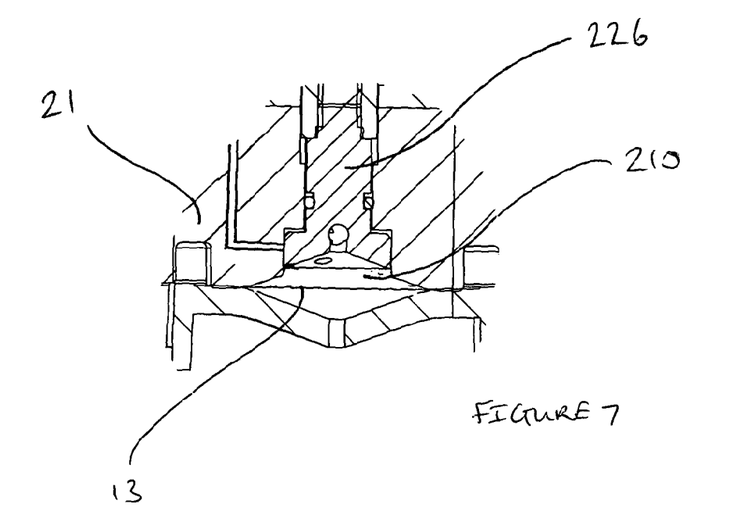
FIG. 7 is detailed view of a part of the sectioned plan view of FIG. 7 showing the piston in a first position.

For example, in the event that the sensor 78 detects that the conductivity of the bicarbonate mixture is too low, and therefore the admixture is too weak the stepper motor is controlled to retract the piston into the plate as shown in FIG. 7. In FIG. 7, the piston 226 is shown in a first position in which the stepper motor 228 has been actuated to draw the piston into the platen 21. This has increased the volume of the bicarbonate dosing pump cavity 210 such that upon actuation of the membrane 13 by the pneumatic valve 234 an increased volume of bicarbonate will be pumped from the chamber. This will then correct the strength of the bicarbonate mixture on subsequent strokes of the pump.

Figure 8:
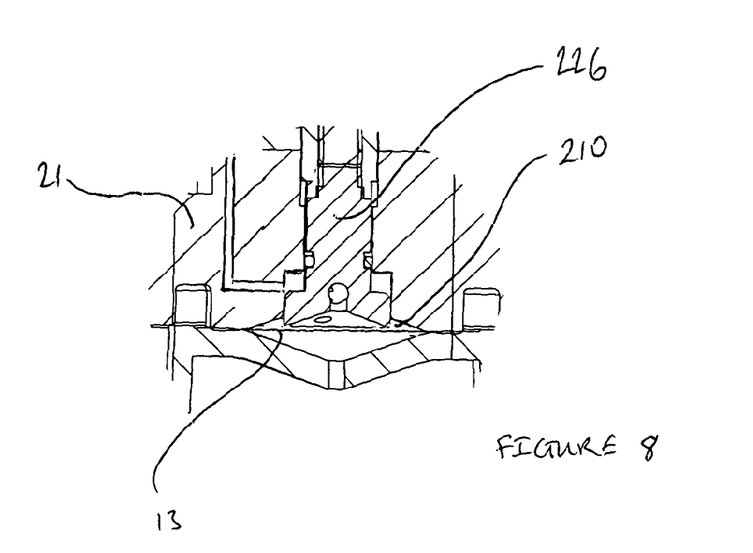
FIG. 8 is detailed view of a part of the sectioned plan view of FIG. 7 showing the piston in a second position.

Conversely, in the event that the sensor 78 detects that the conductivity of the bicarbonate mixture is too high, and therefore the admixture is too strong the stepper motor is controlled to extend the piston into the bicarbonate dosing pump cavity 210, as shown in FIG. 8. In FIG. 8, the piston 226 is shown in a second position in which the stepper motor 228 has been actuated to drive the piston outwardly with respect to the platen 21. This has decreased the volume of the bicarbonate dosing pump cavity 210 such that upon actuation of the membrane 13 by the pneumatic valve 234 a decreased volume of bicarbonate will be pumped from the chamber. This will then correct the strength of the bicarbonate mixture on subsequent strokes of the pump.

Whilst two positions of the piston 226 are shown in FIGS. 7 and 8, the stepper motor 228 can nonetheless be controlled in order to achieve a multitude of positions such that the volume of dialysate pumped can be deliver an accurately controlled by the position of the piston 226.

It will be appreciated that whilst the description above is given in respect of the bicarbonate dosing pump, the same features are provided in the acid dosing pump such that the volume of acid solution pumped from the acid dosing pump chamber 68 into the acid pump chamber 62 can be altered by the position of the piston in the acid dosing pump cavity 212 in response to the conductivity of the fully mixed dialysate measured by the sensor 82.

It will also be appreciated that whilst the example embodiment given above describes mixing pumps in the form of membrane pumps, the invention could equally be used with other forms of mixing pumps currently used in the preparation of dialysate.

The invention claimed is:

1. A hemodialysis machine including
a cartridge which defines a flow path for delivering dialysate fluid to and from a dialyser;
a main body having a platen which, in use, abuts the cartridge;
the cartridge having a chassis with a platen side covered by a deformable membrane which, in use, abuts the platen, the membrane having a first side and an opposite second side, the chassis and the first side of the membrane defining the flow path, the flow path including a first dialysate base solution pump chamber;
the platen and the second side of the membrane defining a first dialysate base solution pump cavity which, collectively with the first dialysate base solution pump chamber, forms a first dialysate base solution pump for pumping dialysate base solution to a first mixing pump chamber by actuation of the membrane, wherein pressure in the first dialysate base solution pump cavity is controlled and applied to the membrane, negative pressure in the first dialysate base solution pump cavity draws the membrane into the first dialysate base solution pump cavity causing fluid to be drawn into the first dialysate base solution pump chamber, and positive pressure in the first dialysate base solution pump cavity pushes the membrane out of the first dialysate base solution pump cavity causing fluid to be pushed out of the first dialysate base pump chamber;
wherein a volume of the first dialysate base solution pump cavity is variable so as to allow a variation in a volume of dialysate base solution pumped from the first dialysate base solution pump chamber to the first mixing pump chamber; and
wherein the positive or negative pressure in first dialysate base solution pump cavity is provided to the first dialysate base solution pump cavity via a pneumatic line through the platen.

2. The machine according to claim 1 wherein the platen further includes a first mixing pump cavity which, collectively with the first mixing pump chamber, forms a first mixing pump for pumping the dialysate fluid to the dialyser.

3. The machine according to claim 1 wherein the first dialysate base solution pump cavity is defined in part by a piston, the piston being moveable with respect to the platen to vary the volume of the first dialysate base solution pump cavity.

4. The machine according to claim 3 wherein the piston is moveable into and out of the first dialysate base solution pump cavity to vary the volume of the first dialysate base solution pump cavity.

5. The machine according to claim 3 wherein the piston is moved by a stepper motor mounted in the main body.

6. The machine according to claim 1 wherein the machine includes a flow balance pump for pumping the dialysate fluid into and out of the dialyser, the flow balance pump defined collectively by at least one flow balance pump chamber in the cartridge and at least one flow balance pump cavity in the platen.

7. The machine according to claim 6 wherein the flow balance pump comprises a first flow balance pump and a second flow balance pump wherein, in operation, one of the first and second flow balance pumps is upstream of the dialyser and the other of the first and second flow balance pumps is downstream of the dialyser.

8. The machine according to claim 1, further comprising:
a second dialysate base solution pump chamber; and
a second mixing pump chamber;
wherein the first mixing pump chamber comprises:
a water inlet for receiving water from a water source;
a bicarbonate base solution inlet for receiving bicarbonate base solution from the first dialysate base solution pump chamber; and
an outlet for pumping out a water/bicarbonate mix; and
wherein the second mixing pump chamber comprises:
a water/bicarbonate mix inlet for receiving the water/bicarbonate mix from the first mixing pump chamber;
an acid base solution inlet for receiving acid base solution from the second dialysate base solution pump chamber; and
an outlet for pumping out the fully mixed dialysate fluid.

9. The machine according to claim 6,
wherein the flow path includes the at least one flow balance pump chamber downstream of the first mixing pump chamber.

10. The machine according to claim 1 wherein the machine further comprises a conductivity sensor in the flow path downstream of the first mixing pump.

11. The machine according to claim 3, wherein the piston is moved in response to a change in conductivity of fluid pumped out of the first mixing pump chamber.

12. The machine according to claim 8, wherein the machine further comprises:
a first conductivity sensor in the flow path downstream of the first mixing pump chamber; and
a second conductivity sensor in the flow path downstream of the second mixing pump chamber.

13. The machine according to claim 8, wherein
the platen and the second side of the membrane define a second dialysate base solution pump cavity which, collectively with the second dialysate base solution pump chamber, forms a second dialysate base solution pump for pumping dialysate base solution to the second mixing pump chamber by actuation of the membrane, wherein pressure in the second dialysate base solution pump cavity is controlled and applied to the membrane, negative pressure in the second dialysate base solution pump cavity draws the membrane into the second dialysate base solution pump cavity causing fluid to be drawn into the second dialysate base solution pump chamber, and positive pressure in the second dialysate base solution pump cavity pushes the membrane out of the second dialysate base solution pump cavity causing fluid to be pushed out of the second dialysate base pump chamber;

a volume of the second dialysate base solution pump cavity is variable so as to allow a variation in a volume of the acid base solution pumped from the second dialysate base solution pump chamber to the second mixing pump chamber;

the first dialysate base solution pump cavity is defined in part by a first piston, the first piston being moveable with respect to the platen to vary the volume of the first dialysate base solution pump cavity;

the second dialysate base solution pump cavity is defined in part by a second piston, the second piston being moveable with respect to the platen to vary the volume of the second dialysate base solution pump cavity; and at least one of the first and second pistons is moved in response to a change in conductivity of fluid pumped out of the second mixing pump.

14. The machine according to claim 1, the main body further comprising a valve for controlling the positive or negative pressure in the first dialysate base solution pump cavity being applied to the membrane.

15. The machine according to claim 14, wherein the pneumatic line extends between the valve and first dialysate base solution pump cavity.

\* \* \* \* \*

UNITED STATES PATENT AND TRADEMARK OFFICE
CERTIFICATE OF CORRECTION

| | | |
|---|---|---|
| PATENT NO. | : 10,076,597 B2 | Page 1 of 1 |
| APPLICATION NO. | : 14/374756 | |
| DATED | : September 18, 2018 | |
| INVENTOR(S) | : Keith Heyes | |

It is certified that error appears in the above-identified patent and that said Letters Patent is hereby corrected as shown below:

On the Title Page

In the name of the Assignee, item (73), delete "Quanta Fluid Systems Ltd." and substitute therefor --Quanta Dialysis Technologies Limited--.

Signed and Sealed this
Fourteenth Day of May, 2019

Andrei Iancu
*Director of the United States Patent and Trademark Office*